United States Patent [19]

Seman

[11] Patent Number: 5,514,662
[45] Date of Patent: May 7, 1996

[54] USE OF AMPHOTERICIN B DERIVATIVES AS PROTEASE INHIBITORS

[75] Inventor: Michel Seman, Paris, France

[73] Assignee: Laboratoires Mayoly Spindler (S.A.R.L.), Chatou Cedex, France

[21] Appl. No.: 87,709

[22] PCT Filed: Nov. 13, 1992

[86] PCT No.: PCT/FR92/01056

§ 371 Date: Nov. 15, 1993

§ 102(e) Date: Nov. 15, 1993

[87] PCT Pub. No.: WO93/09791

PCT Pub. Date: May 27, 1993

[30] Foreign Application Priority Data

Nov. 14, 1991 [FR] France ................... 91 13999

[51] Int. Cl.$^6$ .................................................. A61K 31/70
[52] U.S. Cl. ..................... 514/31; 424/118; 424/119; 536/6.5; 536/115; 549/269; 549/270
[58] Field of Search ................... 536/6.5, 115; 424/118, 424/119; 514/31; 549/269, 270

[56] References Cited

U.S. PATENT DOCUMENTS

| | | | |
|---|---|---|---|
| 5,066,646 | 11/1991 | Driver et al. | 514/31 |
| 5,100,876 | 3/1992 | Driver et al. | 514/31 |
| 5,116,960 | 5/1992 | Driver et al. | 536/6.5 |
| 5,120,718 | 6/1992 | Goldman et al. | 514/32 |
| 5,175,172 | 12/1992 | Dietlin et al. | 514/297 |
| 5,185,366 | 2/1993 | Witiak et al. | 514/456 |
| 5,204,330 | 4/1993 | Driver et al. | 514/31 |

OTHER PUBLICATIONS

Bstracts. STN International, Karlsruhe. AN=CA87(25):193736x. L. S. Kravchenko: "Study of the Proteolytic Activity of Lysosomes from Dog Kidneys Under the Effect of Amphotericin B In Vitro".

Primary Examiner—Douglas W. Robinson
Assistant Examiner—Howard C. Lee
Attorney, Agent, or Firm—Oblon, Spivak, McClelland, Maier & Neustadt

[57] ABSTRACT

The invention is directed toward the use of amphotericin B and derivatives thereof as inhibitors of serine-proteases and for applying these inhibitors for the production of medicinal products intended for the treatment of infection by the human immunodeficiency virus (HIV).

3 Claims, 8 Drawing Sheets

USE OF AMPHOTERICIN B DERIVATIVES AS PROTEASE INHIBITORS

The present invention relates to the use of derivatives of polyene macrolides, in particular amphotericin B, as protease inhibitors, and to the applications of said inhibitors for the production of medicinal products intended in particular for the treatment of infection by the human immunodeficiency virus (HIV).

Since the identification of HIV-1 and HIV-2 as agents for AIDS, numerous research studies have been carried out with the aim of understanding the mechanism of viral infection and of obtaining effective antiviral treatments.

Until now, nucleoside analogues such as AZT (3'-azido-2',3'-dideoxythymidine) and ddI (2',3'-dideoxyinosine) have been used for the treatment of AIDS and have resulted in an improvement of the clinical condition of patients. Unfortunately, severe side effects of treatment with AZT, in particular a degeneration of bone marrow, have been reported, and moreover, many patients do not tolerate the drug very well or they become insensitive to its beneficial effects.

In the case of ddI, its use is still only at the experimental stage and its efficacy requires further investigation.

Furthermore, it has been shown that amphotericin B (AmB) and some of its derivatives are active in vitro against several DNA and RNA viruses containing a lipid envelope, and against various herpes virus strains. The methyl ester of amphotericin B (AME) [SCHAFFNER et al., Biochem. Pharm., 35, 4110–4113, 1986] as well as liposome-encapsulated amphotericin B [PONTANI et al., Antiviral. Res. 11, 119–126 (1989)] have also been described as inhibitors of cell death and of viral expression in T cells infected in vitro with HIV-1. Moreover, since it is known that amphotericin B and its derivatives interact with cellular membrane cholesterol, which causes fluidification of said membranes, it was assumed that this mechanism was responsible for their antiviral activity, either by destroying the virus or by preventing its penetration into the target cells. HANSEN et al. [Antiviral Research, 14, 149–160, (1990)] have studied the in vitro activity of various amphotericin derivatives on the HIV-1 virus. According to the results of this study, AME acts as a cell protecting agent by inhibiting the infection of cells by free HIV: incubation of healthy lymphocytes in the presence of AME prior to infection in vitro with an HIV isolate inhibits the infection; on the other hand, when HIV-infected lymphocytes are preincubated in the presence of AME, their capacity to fuse with uninfected cells so as to form syncytia is increased. Another of the derivatives studied, MCG {N[ N'-(2,4'-methylmorpholino)-N"-ethylguanyl] amphotericin B}, does not possess, according to this study, cell-protecting properties, but has a direct antiviral action: in the case of MCG, it is the preincubation with the virus and not with the cells which inhibits vital infection.

Amphotericin B is currently used in patients suffering from AIDS, in the treatment of infections caused by opportunistic microbes, in particular of deep-rooted mycoses which frequently occur in these patients. Clinical studies have shown that an antifungal therapy has to be maintained indefinitely in order to avoid relapses, or even used as a preventive measure. However, frequent side effects such as fever or serious nephrotoxicity are associated with prolonged treatment using amphotericin B.

By seeking out more active antifungal agents having a reduced toxicity and an enhanced efficacy, the inventors recently obtained, by substituting the mycosamine functional group of amphotericin B by a 1-amino- 1-deoxyketose which can itself be substituted, a series of new derivatives which are more soluble and less toxic than amphotericin B; these derivatives and their use as antifungal agents are the subject of European Patent Application No. 428 440.

In fact, the inventors have now tested the action of some of these derivatives of formula (I) below in which:

R1 represents the macrocyclic portion of the polyene macrolide,

R2 represents a hydrogen atom or a methyl group, and

R3 represents a methyl, ethyl, propyl or phenyl group, as inhibitors of HIV infection.

They have thus observed that these derivatives inhibit the cytopathogenic effects induced by HIV-1, HIV-2 and SIV (simian immunodeficiency virus) and almost completely inhibit the replication of HIV in all the cell types tested, at concentrations substantially below the cytotoxic concentrations.

Experiments carried out by the inventors in order to elucidate the mechanism of action of the derivatives of general formula (I) have shown that they are inactive on reverse transcriptase in vitro, and active on AZT-resistant HIV mutants.

Moreover, the anti-HIV activity of these derivatives exhibits unexpected characteristics in view of the mechanisms of action described in the prior art for other amphotericin B derivatives.

In particular, the inventors have observed that, in contrast to what has been described in the case of AME (HANSEN et al., publication mentioned above), neither the pretreatment of cells with the AmB derivatives of formula (I) before infection, nor the pretreatment of the virus itself, have an inhibitory effect on viral replication.

Moreover, the inventors have observed that the derivatives of formula (I) inhibit the cytopathological effects of the human rhinitis virus (HRV14) in cultures of Hela-Ohio cells; yet, unlike the HIV-1 virus, the HRV14 virus is not an enveloped virus.

The inventors have therefore made the hypothesis that a common mechanism, different from the interaction with the cell membrane cholesterol and/or the viral envelope, may be involved in the anti-HIV and anti-Rhinovirus activities of the derivatives of general formula (I).

Moreover, the inventors have observed that the derivatives of formula (I) constitute protease inhibitors.

Now, the multiplication of HIV-1, like that of the Rhinovirus, requires the action of proteolytic enzymes: in the case of the Rhinovirus, two proteases participate in the maturation of the polyprotein derived from the translation of the viral RNA; in the case of HIV-1, at least one cellular protease may play a role in the fusion between the viral envelope and the cellular membrane, as well as in the formation of syncytia, and a viral protease (protease p10) may participate in the maturation of viral proteins.

The derivatives of formula (I) are inactive in vitro on protease p10, which is an aspartyl protease; in contrast, they are active on trypsin and on other serine proteases.

The inventors have investigated into whether other amphotericin B derivatives possess the same protease-inhibiting activity; they observed that derivatives in which the mycosamine functional group is substituted by a 1-amino-1-deoxyketose group, such as those described in European Application No. 428 440, have an activity similar to that of the derivatives of formula (I); moreover, amphotericin B, as well as all its derivatives which have been tested by the inventors, possess, although to very different degrees, a certain inhibitory activity on trypsin; the extent of this activity seems to be linked to the presence of a substituent on the mycosamine.

The new properties of the amphotericin B derivatives demonstrated by the inventors, and in particular the serine protease-inhibiting properties, make it possible to propose new uses for these derivatives. In particular, those of these derivatives with substantial serine protease-inhibiting activity can be used in the treatment of diseases involving a pathogenic agent whose multiplication cycle requires at least one proteolytic enzyme of the serine protease type.

The subject of the present invention is the use of amphotericin B, or of a derivative thereof, for the production of a protease inhibitor which is active in particular on serine proteases such as trypsin, kallicrein and leucocyte elastase.

According to a preferred embodiment of the present invention, the amphotericin B derivative used is chosen from the derivatives whose trypsin-inhibiting activity is at least twice greater than that of amphotericin B.

According to another preferred embodiment of the present invention, the mycosamine functional group of the amphotericin B derivative used is substituted.

According to a preferred arrangement of this embodiment, the mycosamine functional group is substituted by an aspartyl group.

According to another preferred arrangement of this embodiment, the mycosamine functional group is substituted by a 1-amino-1-deoxyketose group which is itself substituted where appropriate.

According to a preferred form of this arrangement, the derivative used is of the formula (I), in which:
R1 represents the macrocyclic portion of a polyene macrolide, preferably amphotericin B,
R2 represents a hydrogen atom or a methyl group, and
R3 represents a methyl, ethyl, propyl or phenyl group.

The subject of the present invention is also the use of the serine protease inhibitors as defined above for the production of products, in particular medicinal products, which inhibit the multiplication of a pathogenic agent whose multiplication cycle requires the action of at least one proteolytic enzyme of the serine protease type.

The amphotericin B derivatives which are preferred for this use are those whose trypsin-inhibiting activity is at least twice greater than that of amphotericin B.

According to a preferred embodiment of the present invention, the said pathogenic agent is a virus.

According to a preferred arrangement of this embodiment, said virus is the HIV-1 virus.

According to another preferred arrangement of this embodiment, said virus is the HIV-2 virus.

According to another preferred arrangement of this embodiment, said virus is the SIV virus.

According to yet another preferred arrangement of this embodiment, said virus is a Rhinovirus, in particular the human Rhinitis virus.

According to another preferred embodiment of the present invention, said pathogenic agent is a bacterium.

According to another preferred embodiment of the present invention, said pathogenic agent is a eucaryotic organism, a parasite for man or for animals.

The present invention will be more clearly understood by means of the additional description below which refers to detailed examples relating to the evaluation of the protease-inhibiting effect of various amphotericin B derivatives, and of the activity on HIV, SIV and HRV14 of a trypsin-inhibiting derivative, 1-deoxy- 1-amino-4,6-O-benzylidene-D-fructosyl-AmB (termed below DABF-AmB).

However, it is evident that these examples are given solely by way of illustration of the subject of the invention and in no manner constitute a limitation thereof.

I) DETERMINATION OF THE INHIBITORY ACTIVITY OF VARIOUS AMPHOTERICIN DERIVATIVES ON SERINE PROTEASES

1) Inhibition of Trypsin

The different derivatives tested (AmB, AmB-methyl ester (AME), N-acetyl-AmB, N-aspartyl-AmB, N-acetyl-AME, DABF-AmB) were added, at a concentration of 1 µM, to a $3.6 \times 10^{-9}$M solution of trypsin in a 0.1M Tris-HCl buffer, pH 8.2, in the presence of 0.35 mM of DTNB; the reaction is initiated by adding the amount of substrate (Z-lysinthiobenzyl ester) required for a final concentration of $0.6 \times 10^{-6}$M. The reaction is monitored by measuring the optical density at 412 nm.

Figure 1:
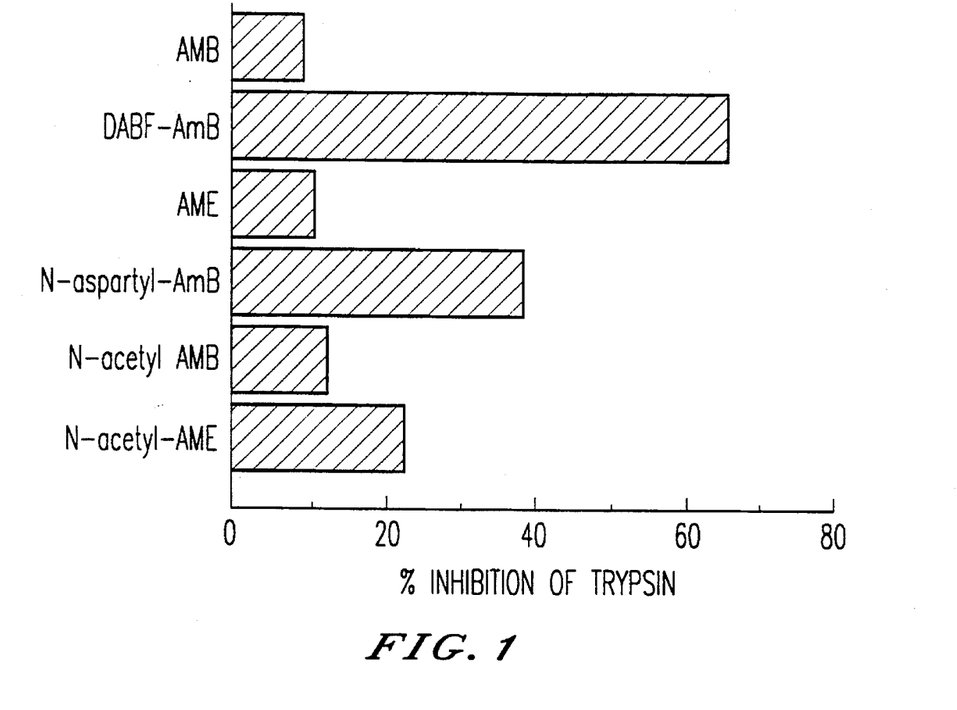

The results are represented in FIG. 1; they are expressed in % inhibition relative to a control without inhibitor. Under the conditions of the experiment, DABF-AmB inhibits the activity of trypsin by more than 60%; the other derivatives tested have some activity (from about 10% inhibition for AmB and AME up to about 40% inhibition for N-aspartyl-AmB), but none possesses an activity comparable to that of DABF-AmB. Moreover, it was shown that benzylidene glucoside alone has no inhibitory action.

Table I shows the inhibition effect of increasing concentrations of DABF-AmB on trypsin. Total inhibition is observed for a concentration of $10^{-4}$M.

TABLE 1

| % OF INHIBITION OF TRYPSIN BY DABF-AmB AND AMB | | | | |
|---|---|---|---|---|
| | $10^{-7}$ M | $10^{-6}$ M | $10^{-5}$ M | $10^{-4}$ M |
| DABF-AmB | 20 | 50 | 95 | 100 |
| AMB | 5 | 10 | 30 | NT* |

*No tested.

These results suggest that the functional group involved in the protease-inhibiting effect is present in the AmB molecule but that it is not accessible as long as the modification of solubility and behavior in solution has not been achieved. The presence of a substituent on the $NH_2$ group of mycosamine appears to increase the inhibitory activity of the molecule.

2) Activity of DABF-AmB on Various Proteases

DABF-AmB was tested, at a concentration of 1 μM, on various proteases (papain, chymotrypsin, kallicrein, leucocyte elastase, cathopsin D and recombinant protease p10) under conditions and in the presence of substrates appropriate for each of the proteases tested.

Figure 2:
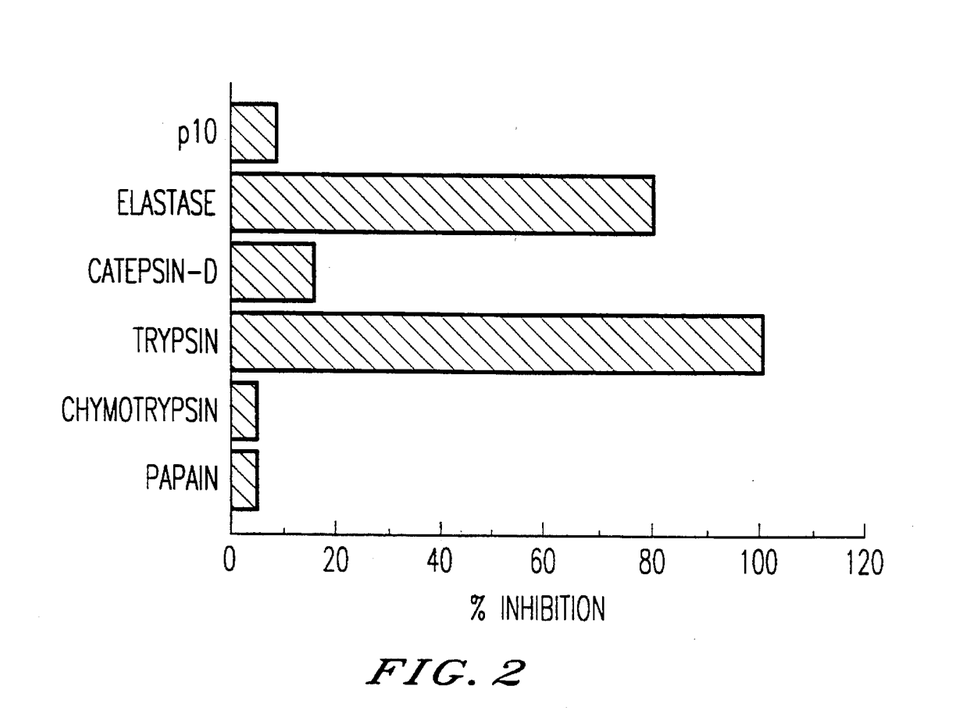

The results are represented in FIG. 2, in percentage of inhibition observed for trypsin under the same conditions. DABF-AmB inhibits kallicrein (results not shown) and leucocyte elastase which, like trypsin, are serine proteases, but in contrast does not inhibit chymotrypsin. DABF-AmB does not inhibit papain (cysteine protease) nor cathopsin D and protease p10 (aspartyl proteases).

An essential component of the activity of DABF-AmB on HIV and SIV viruses is certainly due to its action on the serine proteases of the cellular membrane, which play a part in vital infection.

The measurement of the inhibitory activity of amphotericin B derivatives on a serine protease such as trypsin can constitute a screening method allowing the selection of the derivatives which are most active on HIV.

II) ACTION OF DABF-AmB ON THE HIV AND SIV VIRUSES

GENERAL PROCEDURES

The N-methylglucamine salt of DABF-AmB is prepared as described in European Application No. 428 440. It is dissolved in a 5% sterile solution of glucose in water and then diluted in culture medium.

The T cells (Jurkat and CEM) used are very permissive to HIV infection. They are cultured in RPMI 1640 medium supplemented with 10% foetal calf serum, 2 mM of glutamine and a mixture of penicillin and streptomycin. The peripheral blood mononuclear cells are obtained from blood from healthy donors, isolated on a Ficoll Hypaque gradient and stimulated with 10 μg/ml of phytohaemagglutinin A (PHA), for two days, in RPMI 1640 medium supplemented, prior to the infection by HIV, with amikacin and vancomycin (10 mg/ml), polybrene (1 mg/ml) and anti-interferon gamma serum (5 U/ml). After infection, the PBMCs are cultured ($10^5$ per well) in flat-bottomed 96-well plates in the same RPMI 1640 medium (200 μl per well).

Infectious preparations of the LAV/Bru strain of HIV-1 are obtained from chronically infected CEM cell (clone 13) culture supernatants filtered through a 0.45-μm filter.

For the infection, fresh Jurkat or CEM type cells are centrifuged and the pellet is incubated for 2 hours at 37° C. with the viral preparation (10000 cpm of reverse transcriptase activity/$10^6$ cells, which corresponds to a multiplicity of infection of 0.04 to 0.1). The cells are then washed and resuspended ($0.5 \times 10^{6}$/ml) in fresh culture medium. Reverse transcriptase activity is determined at specific times after the infection, using the acellular infected cell supernatant.

The PBMCs cells ($2 \times 10^6$/ml) are infected with the same viruses and under the same conditions as the Jurkat or CEM cells. They are then washed and resuspended in fresh culture medium in flat-bottomed 96-well plates ($10^5$ cells per well in 200 ml).

The reverse transcriptase activity is determined at the indicated times using the culture supernatant, according to the procedure described by REY et al., Biochem. Res. Comm. 121, 126–133 (1984).

The viral antigen p24 was quantified in the infected-cell supernatant by radioimmunological assay using the procedure recommended by the manufacturer (ABBOTT, Diagnostics Division).

Membrane expression of CD4 and gp120 is measured by means of the monoclonal antibodies OKT4 (0,5 μg/ml), 110-4 (2 μg/ml) respectively, which are stained using a goat antibody to fluorescein isothiocyanate-conjugated mouse Ig.

The fluorescence is measured by means of a FACSTAR cell counter (BECTON DICKINSON, MOUNTAIN VIEW, Calif.). The results are expressed as mean fluorescence intensity.

The CD4-specific monoclonal antibody (OKT4 was bought from ORTHO PHARMACEUTICAL CORPORATION (Raritan, N.J.).

The anti-gp110 monoclonal antibody 110-4 (GENETIC SYSTEMS CORP., Seattle, Wash.) also recognizes gP120 at the surface of the T cells.

EXAMPLE 1—Action on Reverse Transcriptase Activity

The Jurkat and CEM type T cells are infected with the LAV/BRU strain of HIV-1.

Viral infection and replication are monitored by measuring the reverse transcriptase activity in the culture supernatants.

As shown in FIG. 3, the reverse transcriptase activity can be detected from the 4th day of the infection for both cell types and a large activity peak, at $3.2 \times 10^6$ and $1.5 \times 10^6$ cpm/ml, is observed on the 7th and 8th day after the infection, in the Jurkat (FIG. 3a) and CEM (FIG. 3c) cells respectively. The reverse transcriptase activity then decreases down to a plateau (about $0.2$–$0.4 \times 10^6$ cpm/ml). This plateau remains stable for more than 2 months, and reflects a chronic infection of the T cells. The infected cells remain viable and within two months following the infection, no substantial cell death or inhibition of cell growth are observed.

To measure the anti-HIV activity of DABF-AmB, infected cells are cultured in the presence of increasing doses (between 0.1 μM and 100 μM) of the product; the latter is added immediately after inoculation and the concentrations are kept constant during the infection by carrying out a one half dilution, every 3 days, of the growing cells in fresh medium containing the desired concentration.

Figure 3A:
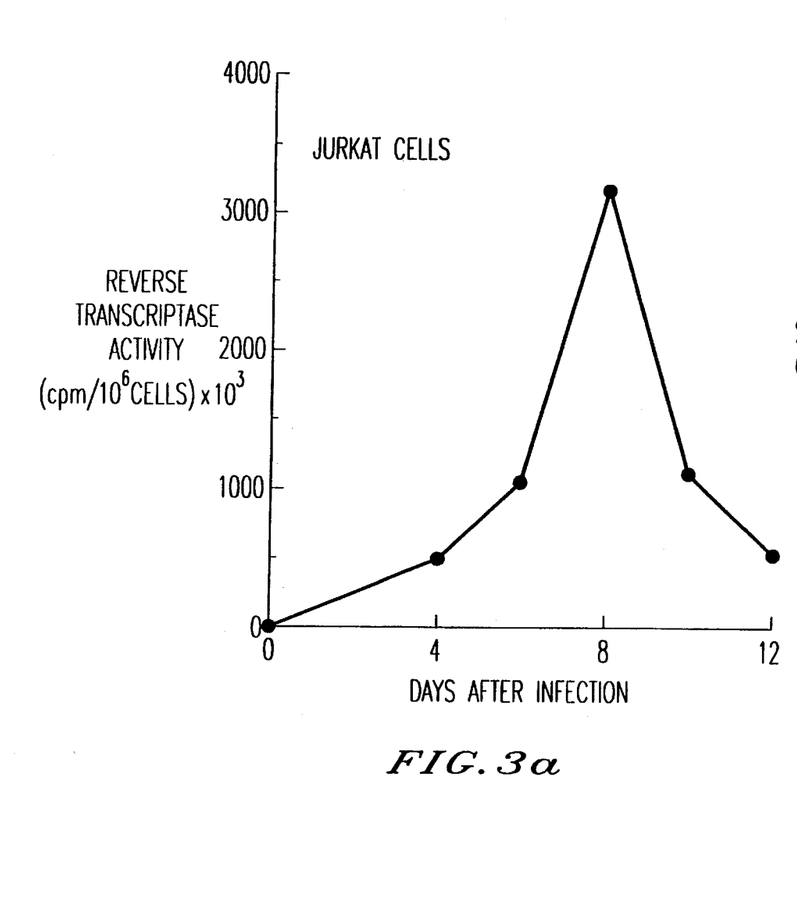
Figure 3B:
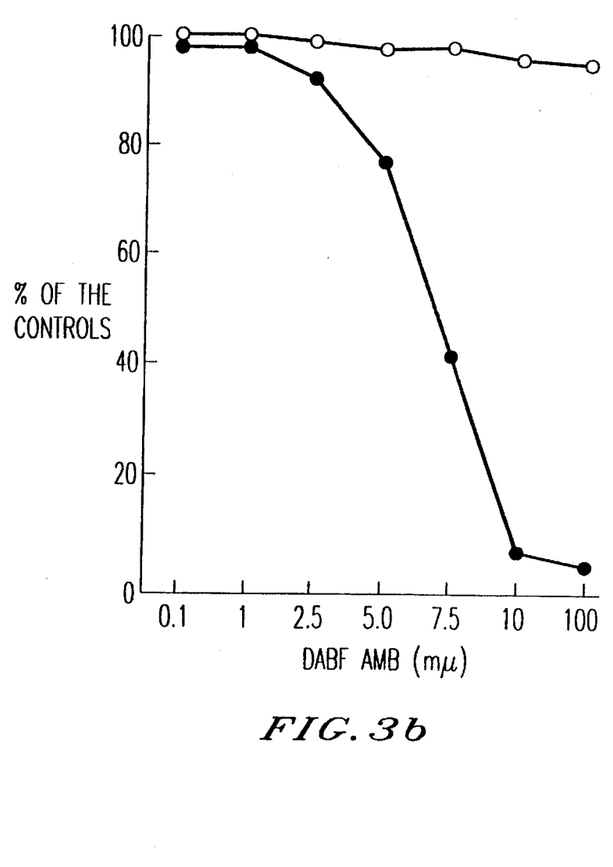
Figure 3C:
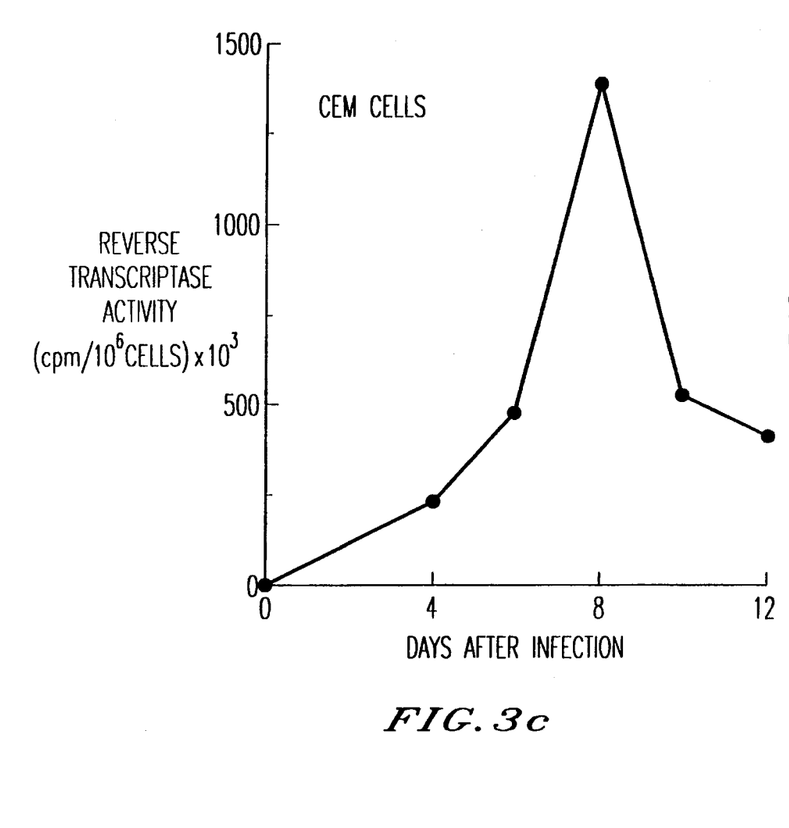
Figure 3D:
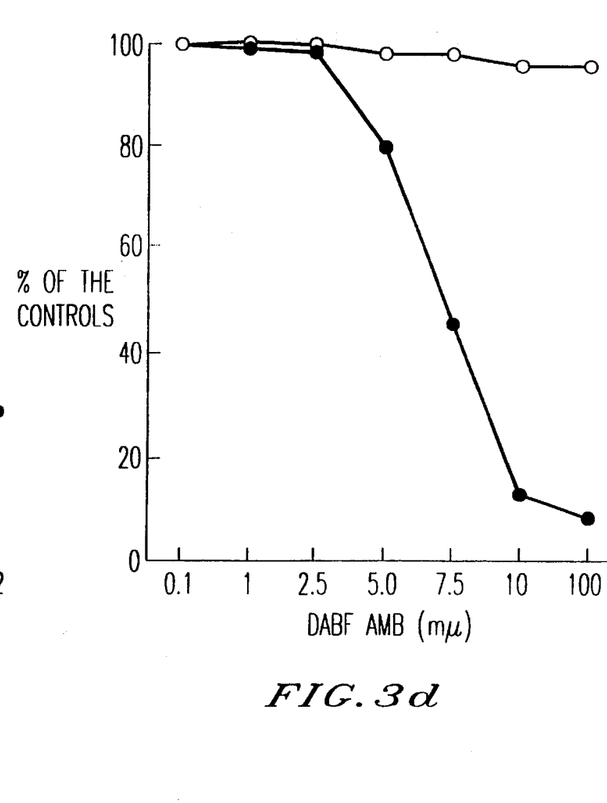

The corresponding results are illustrated in FIGS. 3b and 3d: the reverse transcriptase activity measured on the 8th day of the viral infection is represented on the y axis and the DABF-AmB concentration on the x axis.

Inhibition of reverse transcriptase activity is observed both in the Jurkat cells (FIG. 3b) and in the CEM cells (FIG. 3d) from 5 μM upwards and the activity is completely inhibited (inhibition of 88%, N=4) at 10 μM of DABF-AmB. The latter concentration was therefore chosen for the rest of the studies on the anti-HIV activity of the product. No significant inhibition was observed for DABF-AmB concentrations below 1 μM.

Cell viability was estimated at the same time. At concentrations above 100 μM, no cytotoxic effect was observed for DABF-AmB either on the Jurkat cells or on the CEM cells. It therefore appears that DABF-AmB inhibits the replication of HIV at doses which are not cytotoxic.

It was shown that DABF-AmB has no direct action on reverse transcriptase activity and that, consequently, the decrease in this activity cannot be due to a direct inhibition of the enzyme by DABF-AmB.

EXAMPLE 2—Action on the Expression of the Soluble Viral Antigen p24

The expression of the soluble viral antigen p24 was investigated at the same time as the reverse transcriptase activity, in the cell culture supernatants.

The untreated Jurkat cells as well as the untreated CEM cells produce large amounts of p24 on the 8th day after the infection.

Likewise, as for the reverse transcriptase activity, the continuous addition of DABF-AmB at a concentration of 10 µM, kept constant for 12 days after the infection, substantially decreases the amount of p24 antigen (88% inhibition, N=3) in both cell lines.

Figure 4A:
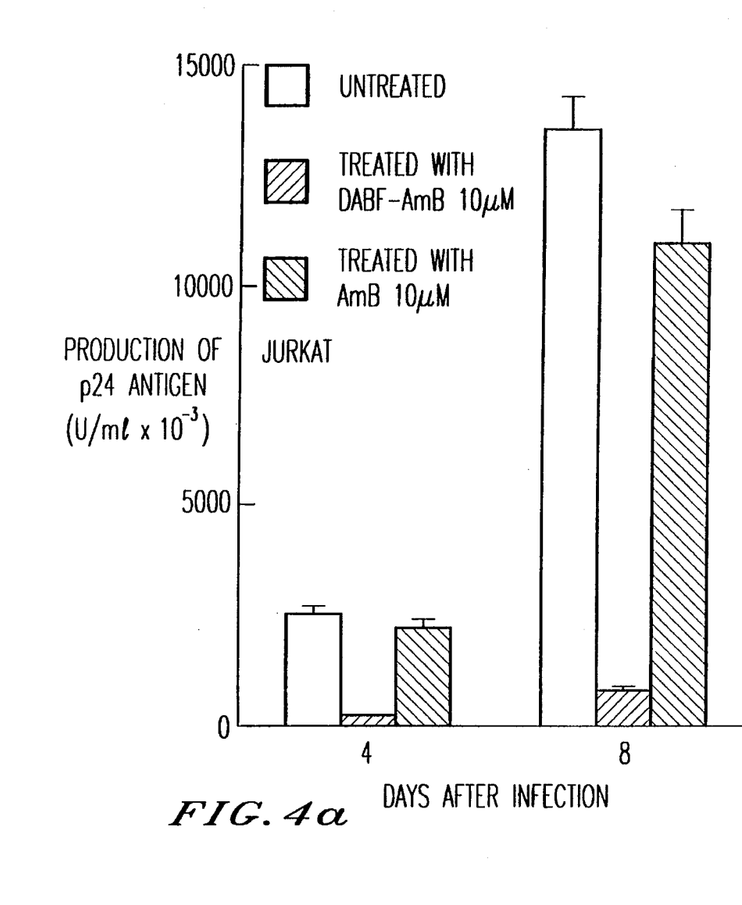
Figure 4B:
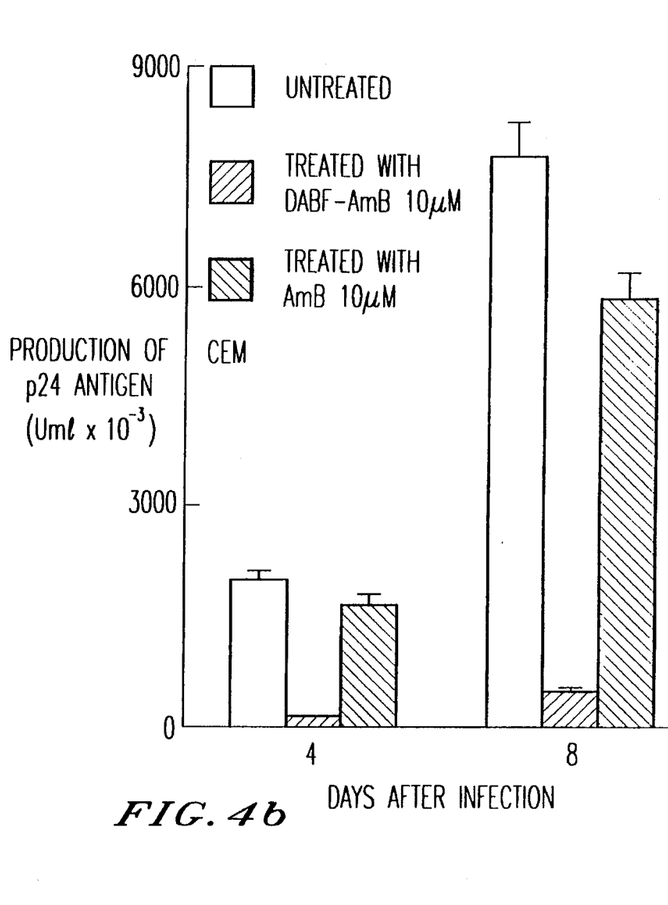

These results are illustrated in FIG. 4, which represents the production of antigen p24, 4 days and 8 days after the infection:

■ Untreated infected cells

▨ DABF-AmB-treated cells

▨ AmB-treated cells (10 µM)

The AmB treatment is carried out under the same conditions as the DABF-AmB treatment. These results show that the efficacy of DABF-AmB on the multiplication of HIV is substantially greater than that of AmB.

A significant inhibition is observed for DABF-AmB concentrations greater than 5 µM.

In another experiment, 10 µM of DABF-AmB are added either during pretreatment 24 hours before the infection, or alternatively during the 2-hour inoculation stage, or alternatively during continuous treatment, as described above, for 12 days following the infection. In this case, the addition of DABF-AmB prior to the infection, or alternatively during the 2-hour stage corresponding to viral adsorption, does not bring about any significant inhibition of p24 secretion or of reverse transcriptase activity.

EXAMPLE 3—Action on the Expression of the Viral Antigen gp120 and the Cellular Antigen CD4

The replication of HIV-1 can also be monitored by the expression of the envelope glycoprotein gp120 at the surface of the infected cells, as well as by the decrease in the membrane antigen CD4.

Immunofluorescence analyses are carried out on the 8th day of the infection in order to verify whether the inhibition of HIV replication by DABF-AmB results in 10 a reduced membrane expression of viral antigens.

On the 8th day of the infection, high levels of gp120 and low levels of CD4 are observed in the untreated Jurkat and CEM cells (which is verified by the use of the monoclonal antibodies 110.4 and OKT4 respectively).

Continuous treatment with 10 µM of DABF-AmB substantially reduces membrane expression of gp120 in both cell lines. At the same time, the level of the membrane antigen CD4 in the DABF-AmB-treated infected cells increases until it reaches that for the uninfected cells.

The level of the membrane antigen CD3 is unchanged in the treated or untreated infected cells.

EXAMPLE 4—Action of DABF-AmB on the Replication of HIV in PBMCs

PBMCs isolated from healthy individuals are infected with HIV-1. The production of antigen p24 as well as the reverse transcriptase activity can be detected in the supernatants of cultures infected 3 days after the infection. The maximum reverse transcriptase activity and p24 synthesis are observed between the 6th and 7th day, and the 5th and 6th day respectively. No cell death is observed at this time.

The infected PBMCs are treated continuously as described above for the Jurkat and CEM cells, using increasing concentrations of DABF-AmB.

The effect of DABF-AmB on the reverse transcriptase activity and on the secretion of p24 is evaluated on the 6th day.

As in the case of Jurkat and CEM cells, the product almost completely inhibits the reverse transcriptase activity as well as the syntheses of p24 (92±4 and 88±6% inhibition respectively, N=3) at a concentration of 10 µM.

Concentrations below 1 µM produce only a low inhibition whereas concentrations above 20 µM do not bring about a significant increase in the anti-HIV action.

Moreover, DABF-AmB is without cytotoxic effect on PBMCs at concentrations ranging up to $10^{-3}$M.

It therefore appears that DABF-AmB effectively inhibits the replication of HIV-1 in normal human T cells at non-cytotoxic concentrations.

EXAMPLE 5—Protection, by DABF-AmB, of CD4 Cells in Cultures of HIV-infected Human Thymocytes Human thymuses were obtained during corrective heart surgery operations on 3 to 7 year old children. The tissues were cut into fragments and the red blood cells were removed by treating with Tris-$NH_4Cl_2$ buffer. After washing in PBS buffer, cellular suspensions were prepared in an RPMI 1640 medium containing 10% of human serum type AD. Dead cells were removed by passing over a sterile nylon wool column.

The cells were infected with HIV LAV/BRU as indicated above in the general procedures, and then re-inoculated in the presence of PHA, of anti-CD2 or anti-CD 3 antibodies and of IL2 and cultured for 10 days at a rate of $1 \times 10^7$ cells/ml. After 10 days, viral production was evaluated by measuring the RT activity in the supernatants and the distribution of CD4/CD8 was evaluated by double fluorescence flow cytometry by means of FITC-labelled anti-CD4 antibodies (OKT4) and phycoerythrin-labelled anti-CD8 antibodies (OKT8). DABF-AmB was added to the cultures immediately after infection and maintained during the entire duration of the culture.

DABF-AmB does not significantly modify, even at 10 µM, the distribution of the CD4 and CD8 cells in cultures of uninfected thymocytes activated with PHA or with anti-CD2 or anti-CD3 antibodies. A slight increase in the CD4+ CD8+ population is just about observed.

In the infected and uninfected cultures, a substantial decrease is observed in the CD4+CD8+ population and in the CD4+CD8- population in correlation with a high viral production. In the presence of DABF-AmB, the preservation or the reappearance of CD4+ cells in the infected cultures, in proportion to the concentration of the product. This reappearance or this preservation of CD4+ cells are in correlation with a decrease in RT activity in the supernatants.

DABF-AmB therefore inhibits the infection of CD4+ thermocytes by HIV and restores a normal distribution of the subpopulations of thymic cells in the infected cultures.

EXAMPLE 6—Action of DABF-AmB on the Early Phases of HIV Infection

HeLa cells transfected with the CD4 gene and capable of being infected by HIV, carrying the bacterial gene LacZ placed under the control of the LTR of HIV [ROCANCOURT et al., J. Virol., 64:2660–2668, (1990)], were infected with HIV-1BRU. 24 hours after the infection of monolayer cultures of H12 cells in 1-ml wells, at various viral doses and in the presence of various concentrations of DABF-AmB, transactivation of the LTR gene by the Tat gene of the virus was revealed by the detection of blue colonies resulting from the activation of β-galactosidase of the LacZ gene. This detection was carried out after fixing the cells by incubating for one hour in-the presence of 5-bromo-4-chloro-3-indoyl-β-D-galactopyranosidase and enzyme substrate. At the concentration of 10 μM, DABF-AmB completely inhibits the appearance of blue colonies, indicating that the product acts early on in the infection cycle.

EXAMPLE 7—Inhibition, by DABF-AmB, of the Cytopathogenic Effects Induced in HUT78 Cells Infected with the Viruses SIVmac251 and HIV-2-nod HUT78 cells were inoculated in 96-well plates in an amount of $2\times10^4$ cells per well, in RPMI 640 medium. They were infected with various viral concentrations and DABF-AmB was added immediately after the infection, at various concentrations. The formation of syncytia was evaluated after 3 and 5 days by direct reading under an inverted microscope (semi-quantitative test).

As indicated in Tables II(infection with HIV-2) and III-(infection with SIV), DABF-AmB inhibits (–) in a dose-dependent manner and as a function of the viral content the formation of syncytia in the cultures (+). It is therefore active on the cytopathogenic effects induced by HIV-2 and by SIV.

TABLE II

ANTIVIRAL EFFECTS OF THE COMPOUND DABF-AmB EVALUATED ON THE CELL LINE HUT78 INFECTED WITH HIV2-rod.

| DABF-AmB/HUT78/HIV2 | Controls | | | | 10 TCID50 | | | | 100 TCID50 | | | |
|---|---|---|---|---|---|---|---|---|---|---|---|---|
| | 1 | 2 | 3 | 4 | 5 | 6 | 7 | 8 | 9 | 10 | 11 | 12 |
| neg./pos control | – | – | – | – | ++ | + | + | ++ | ++ | +++ | ++ | +++ |
| 100 μM | – | – | – | – | high cytotoxicity | | | | – | – | – | – |
| 50 μM | – | – | – | – | low cytotoxicity | | | | – | – | – | – |
| 10 μM | – | – | – | – | – | – | – | – | + | + | – | – |
| 5 μM | – | – | – | – | – | + | – | + | + | + | + | + |
| 1 μM | – | – | – | – | ++ | + | + | ++ | +++ | ++ | ++ | +++ |
| 0.5 μM | – | – | – | – | ++ | ++ | + | + | +++ | ++ | ++ | +++ |
| 0.1 μM | – | – | – | – | + | + | ++ | + | +++ | ++ | +++ | +++ |
| | | | | | Reading after 3 days | | | | | | | |
| neg./pos control | – | – | – | – | ++ | + | ++ | ++ | +++ | +++ | +++ | +++ |
| 100 μM | – | – | – | – | cytotoxicity | | | | – | – | – | – |
| 50 μM | – | – | – | – | – | – | – | – | – | – | – | – |
| 10 μM | – | – | – | – | – | – | – | – | + | ++ | – | – |
| 5 μM | – | – | – | – | – | + | – | + | ++ | ++ | + | + |
| 1 μM | – | – | – | – | +++ | +++ | ++ | ++ | +++ | +++ | +++ | +++ |
| 0.5 μM | – | – | – | – | ++ | ++ | ++ | ++ | +++ | +++ | +++ | +++ |
| 0.1 μM | – | – | – | – | + | + | ++ | ++ | +++ | +++ | +++ | +++ |
| | | | | | Reading after 5 days | | | | | | | |

TABLE III

ANTIVIRAL EFFECTS OF THE COMPOUND DABF-AmB EVALUATED ON THE CELL LINE HUT78 INFECTED WITH SIVmac251

| DABF-AmB'/HUT78/SIV | Controls | | | 10 TCID50 | | | 100 TCID50 | | | 500 TCID50 | | |
|---|---|---|---|---|---|---|---|---|---|---|---|---|
| | 1 | 2 | 3 | 4 | 5 | 6 | 7 | 8 | 9 | 10 | 11 | 12 |
| neg./pos control | − | − | − | − | − | − | + | + | + | ++ | ++ | + |
| 100 μM | − | − | − | − | high cytotoxicity | | − | − | − | − | − | − |
| 50 μM | − | − | − | − | low cytotoxicity | | − | − | − | − | − | − |
| 10 μM | − | − | − | − | − | − | − | − | − | − | − | − |
| 5 μM | − | − | − | − | − | − | − | − | + | − | + | − |
| 1 μM | − | − | − | − | − | − | + | + | + | ++ | + | ++ |
| 0.5 μM | − | − | − | − | − | − | + | + | + | + | ++ | + |
| 0.1 μM | − | − | − | − | − | − | + | + | + | + | ++ | + |
| | | | | | | | Reading after 3 days | | | | | |
| neg./pos control | − | − | − | + | + | + | + | + | + | +++ | +++ | +++ |
| 100 μM | − | − | − | − | cytotoxicity | | − | − | − | − | − | − |
| 50 μM | − | − | − | 31 | − | − | − | − | − | − | − | − |
| 10 μM | − | − | − | − | − | − | − | − | + | − | + | + |
| 5 μM | − | − | − | − | − | + | − | − | + | + | + | − |
| 1 μM | − | − | − | + | + | + | + | ++ | + | +++ | ++ | +++ |
| 0.5 μM | − | − | − | + | + | + | + | + | ++ | ++ | +++ | ++ |
| 0.1 μM | − | − | − | + | + | + | ++ | + | + | + | +++ | +++ |
| | | | | | | | Reading after 5 days | | | | | |

EXAMPLE 8—Inhibition, by DABF-AmB, of the Infection of PBMCs by Various HIV-1 and by AZT-resistant Viruses PBMCs were infected under the conditions described above in the general procedures, with various HIV-1 isolates derived from patients, or identified as resistant to AZT. The anti-viral effect of DABF-AmB was determined by measuring the RT activity in the supernatants after 10 days of culture.

Figure 5:
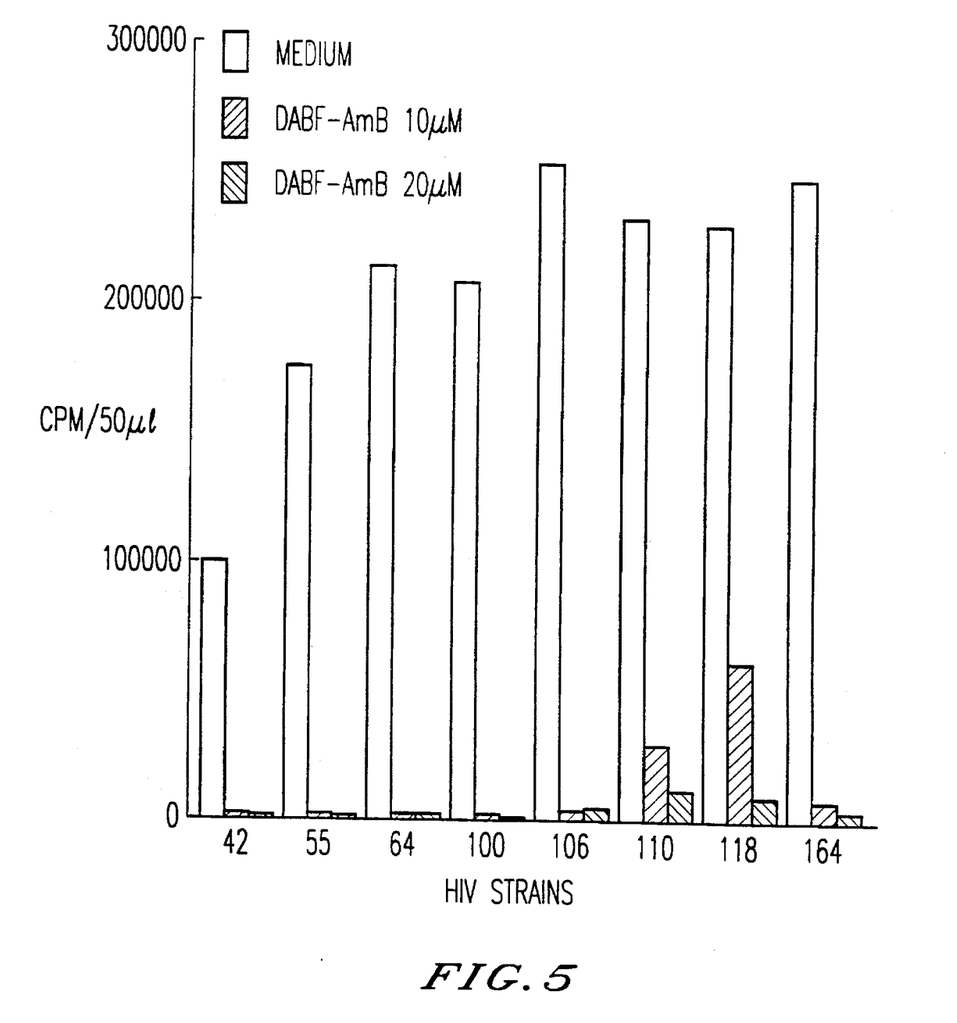
Figure 6A:
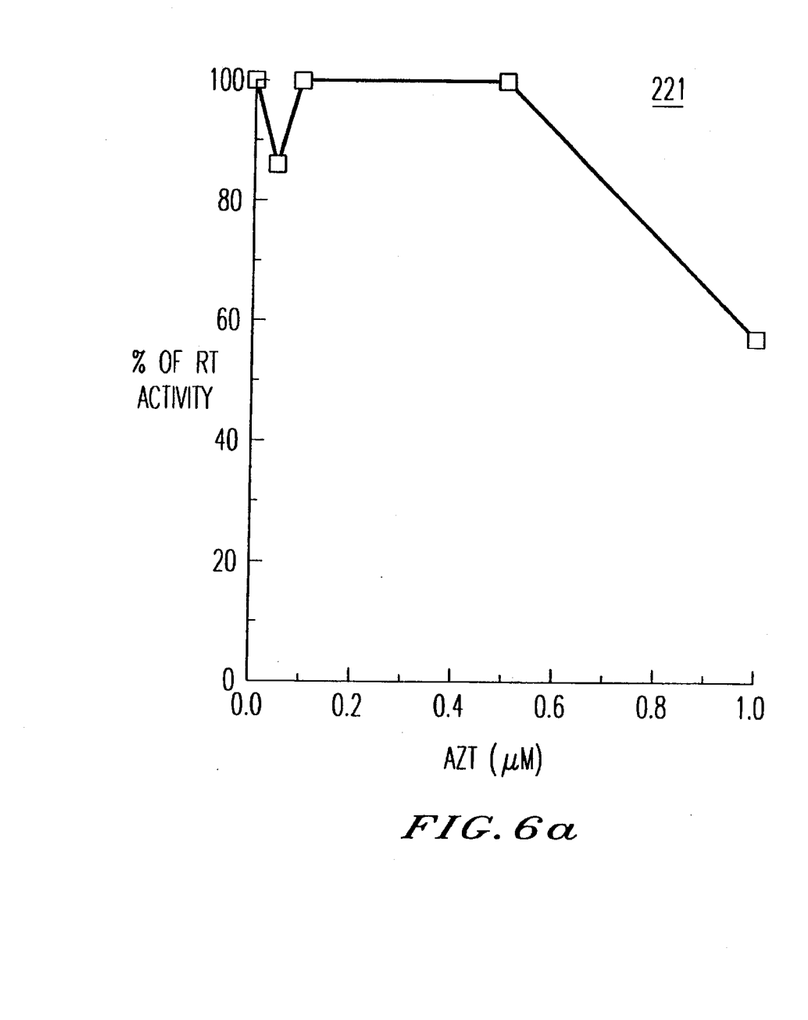
Figure 6B:
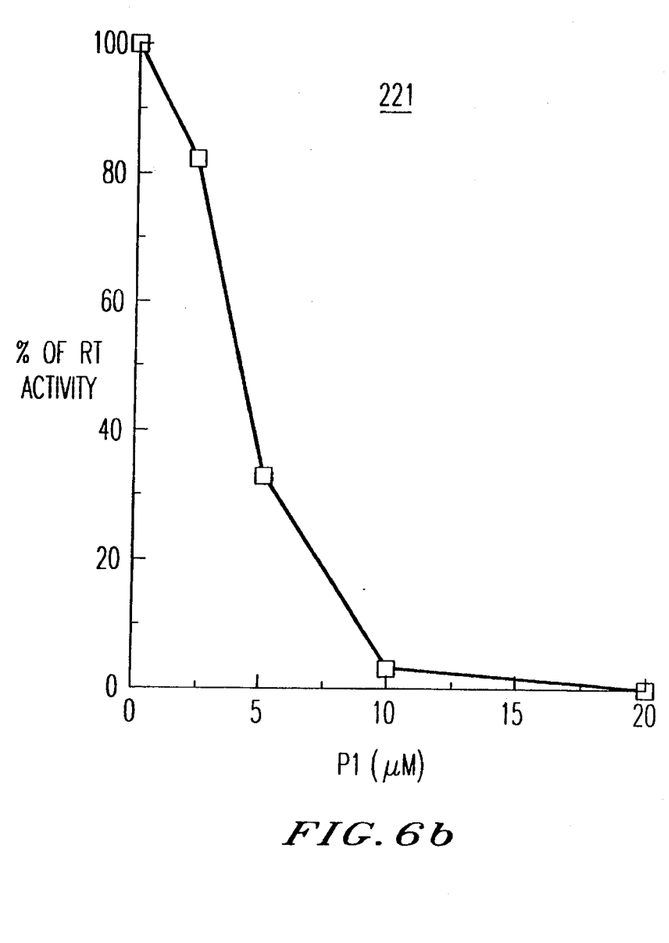
Figure 6C:
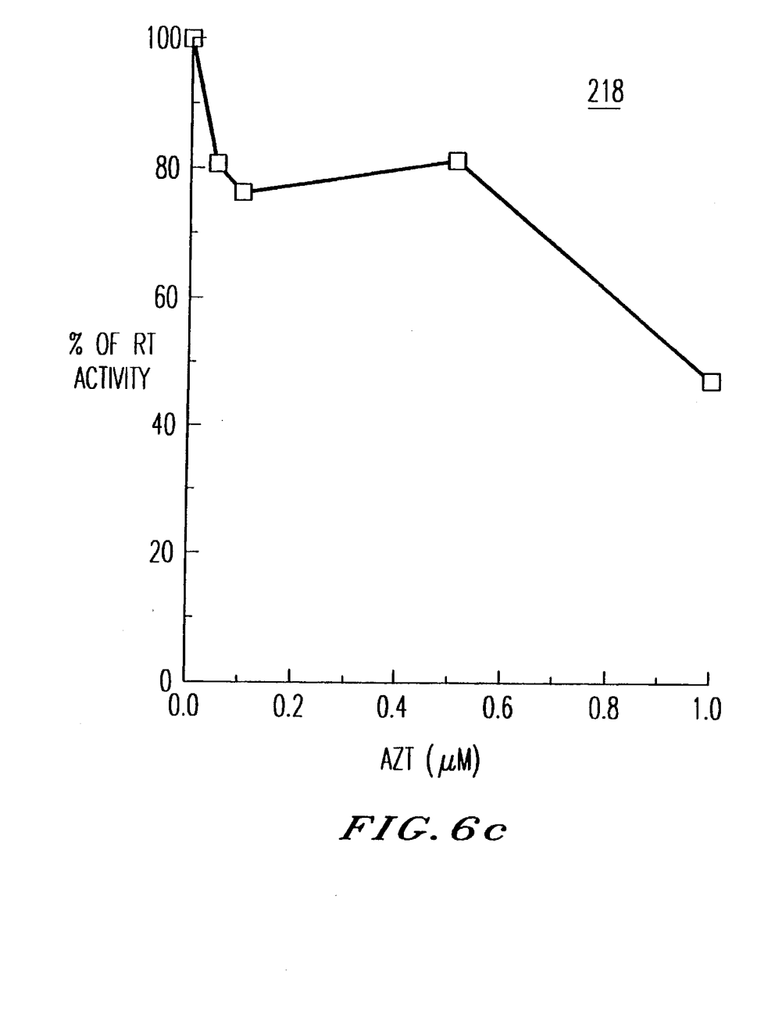
Figure 6D:
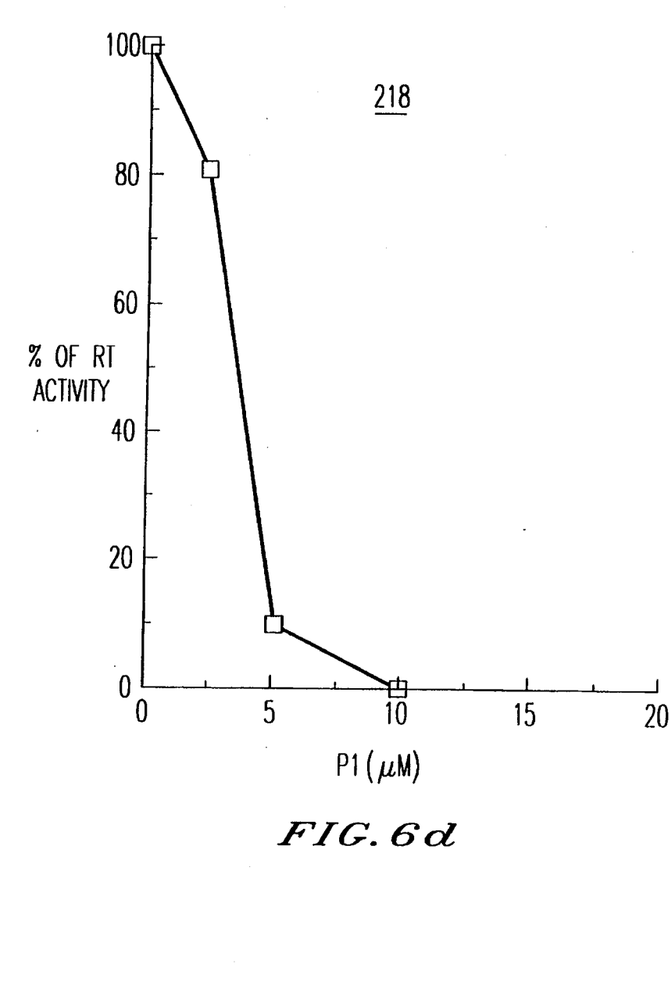
Figure 6E:
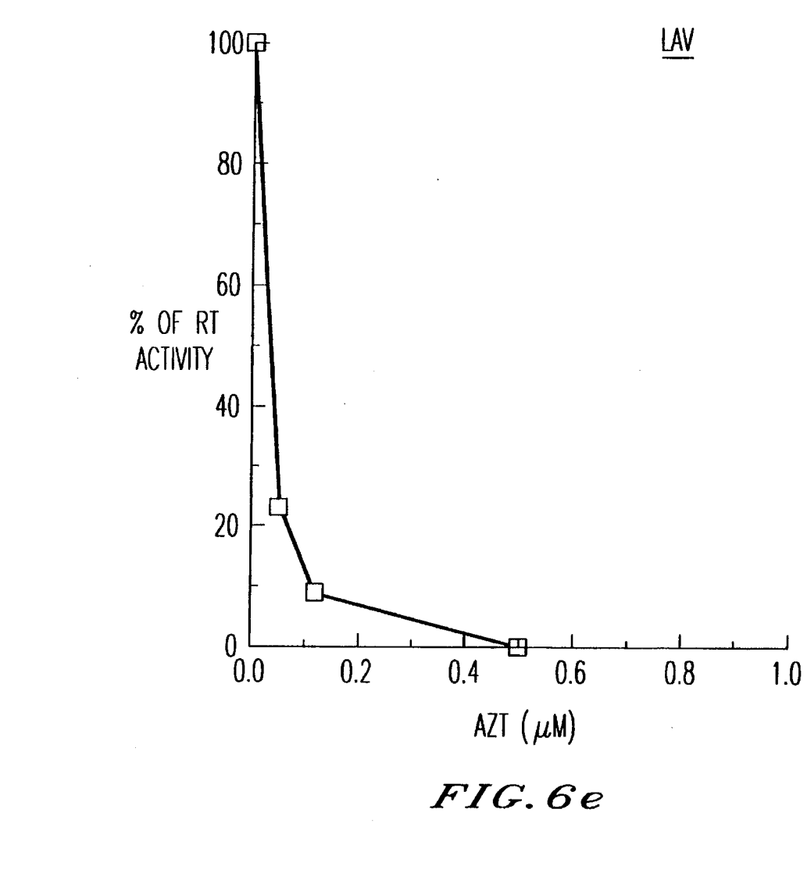
Figure 6F:
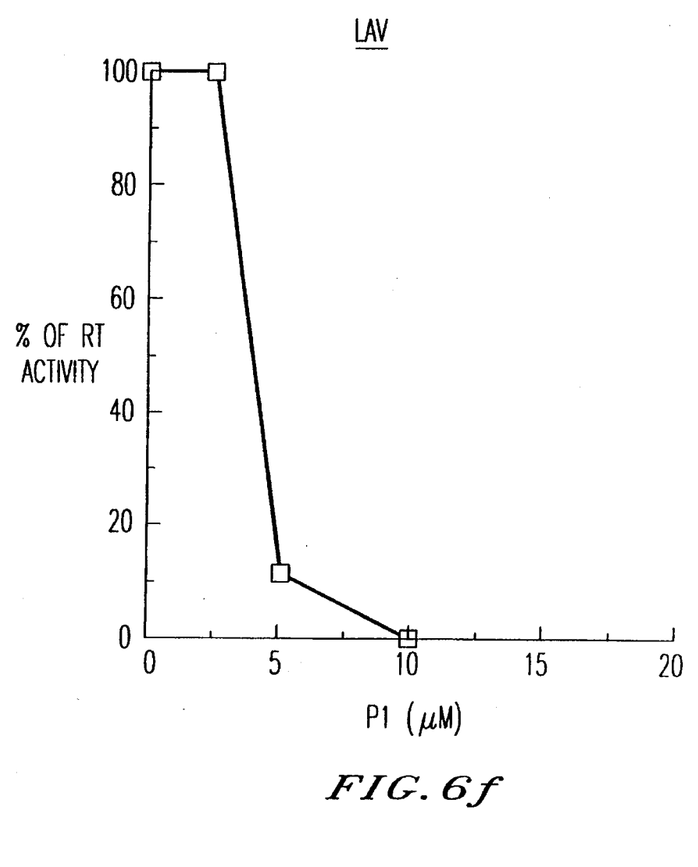

As shown in FIG. 5, DABF-AmB, at 10 μM, is capable of substantially reducing, or even completely inhibiting the infection of PBMC by 10 viral strains derived from patients. FIG. 6 shows that this inhibition is also produced in the case of AZT-resistant strains.

EXAMPLE 9—Inhibition of Cellular Viraemia by DABF-AmB

Lymphocytes from AIDS patients (<200CD4) are isolated on a Ficoll gradient using heparinised blood. The cells are taken up in RPMI 1640 medium containing antibiotics, 10 U/ml of recombinant IL2 (Boeringher) and anti-interferon alpha serum (anti-IFNα, Sigma) plus 10% of foetal calf serum. The cells are cultured in 24-well plates in an amount of $5 \times 10^5$ cells per well for the first concentration and then subjected to 5 fold serial dilutions in the same medium. Half of the medium is replaced twice weekly. Every week, $3 \times 10^5$ fresh allogeneic PBMCs, derived from healthy donors, are added to the cultures. The cultures are kept for 28 days in the presence of varying concentrations of DABF-AmB. Vital production is measured weekly by assaying the protein p24 in the supernatants. Each culture and each assay are carried out in duplicate.

Table IV shows the results obtained for 8 different patients. The symbols (−) denote that the amount of p24 detected is at least 95% less than the values obtained in the untreated control cultures. These results show that the DABF-AmB molecule inhibits cellular viraemia in 7 out of 8 patients. The results obtained in the LOU patient indicates either a resistance of the virus to the product, or a too high initial viral content. These experiments made it possible to evaluate the $IC_{50}$ for DABF-AmB at between 1 and 5 μM for the different viral isolates (IC50=Concentration of the product inhibiting 50% of the p24 titer in the culture supernatants, for a patient cells dilution corresponding to a viral content equivalent to $10TCID_{50}$.

TABLE IV

EFFECT OF DABF-AmB ON CELLULAR VIRAEMIAS

| DAY | RIF | RIF + MS | PHU | PHU + MS | LOU | LOU + MS | VUL | VUL + MS | MAI | MAI + MS | VAC | VAC + MS | CAM | CAM + MS | SAM | SAM + MS |
|---|---|---|---|---|---|---|---|---|---|---|---|---|---|---|---|---|
| 0 | − | − | − | − | − | − | − | − | − | − | − | − | − | − | − | − |
| 7 | + | − | + | − | + | − | + | − | ++ | − | | | | | | |
| 14 | ++ | − | ++ | − | ++ | ++ | ++ | − | | | ++ | − | ++ | − | +/− | − |
| 21 | ++ | − | ++ | − | ++ | ++/− | ++ | − | | | | | | | | |
| 28 | ++ | − | ++ | − | ++ | ++/− | ++ | − | | | | | | | | |

EXAMPLE 10—Action of DABF-AmB on Viral Expression in Reactivated Infected Cells The activation of infected CD4+ cells is known to stimulate the production of the virus. The effect of DABF-AmB was therefore tested on the vital expression in cells from AIDS patients reactivated in vitro by anti-CD3, by anti-CD28, by PMA (phorbol myristate acetate) or by soluble anti-CD3.

PBMCs from patients (<300 CD4) were isolated on a Ficoll gradient using blood. The CD4 cells were isolated by cell sorting using a flow cytometer (FACS-Star, Becton-Dickinson, Mountain View, Calif.) after OKT4-FITC labelling. The CD4 cells were washed again and then re-inoculated as indicated in 5 and activated either with anti-CD3 or anti-CD28 antibodies or with PMA. Viral expression was evaluated after 10 days by ELISA assay of p24 in the supernatants.

The results presented in Table 4 show that in 7 patients tested, DABF-AmB inhibits viral expression by more than 90% at a concentration of 10 µM. These results show that DABF-AmB is capable of inhibiting virus production during reactivation of preinfected cells.

When the suspension of HRV14 is preincubated at 37° C. in the presence of DABF-AmB for 5 hours, no inhibition of the cytopathogenic effect is observed compared with a control suspension incubated under the same conditions in the absence of DABF-AmB. DABF-AmB therefore has no direct virucidal effect on HRV14.

The effect of the addition of DABF-AmB was tested at various times: preincubation of the cells with DABF-AmB before the viral infection; addition of DABF-AmB at the time of the infection; addition of DABF-AmB after the infection, during the period of viral proliferation. The results obtained show that DABF-AmB acts essentially during viral proliferation.

As evident from the above, the invention is not in the least limited to those of its embodiments and applications which

TABLE V

STUDY OF HIV PRODUCTION IN VITRO REACTIVATED CD4 PERIPHERAL BLOOD T CELLS FROM SEROPOSITIVE PATIENTS

| PATIENTS | STIMULATION | | | | | | | | | |
|---|---|---|---|---|---|---|---|---|---|---|
| | cCD3 | cCD3 + MS | CD28 | CD28 + MS | cCD3 ° CD28 | cCD3 + CD28 + MS | PMA | PMA + MS | sCD3 | sCD3 + MS |
| S23 (PP) | | | | | | | + | − | | |
| S24 (I) | | | | | | | +/− | − | | |
| S25 (PP) | | | | | | | | | | |
| S26 (PP) | +/− | | | | ++ | − | | | | |
| S27 (PP) | | | | | | | | | | |
| S28 (PP) | | | | | | | | | | |
| S29 (I) | | | | | + | − | | | | |
| S30 (I) | +/− | − | ++ | | ++ | − | | | | |
| S31 (PP) | | | + | − | | | | | | |
| S32 (PP) | + | − | ++ | − | + | − | | | + | +/− |
| S33 (I) | | | | | | | | | | |
| S34 (PP) | | | | | | | | | | |
| S35 | | | | | | | | | | |
| S36 | | | | | | | | | | |

II)—ACTION OF DABF-AmB ON THE RHINOVIRUS HRV14

EXAMPLE 11—Inhibition, by DABF-AmB, of the cytopathogenic effects of HRV14

HeLa-Ohio cells cultured until they have become confluent, are infected with a suspension of HRV14 virus. The cytopathogenic effect of the virus is evaluated by staining the cells with a 0.5% solution of crystal violet and 20% of methanol; after rinsing the plates with water, the optical density is read at 550 nm.

For the rest of the experiment, the cells are infected with a viral suspension with a titre such that 50% of the cells are killed after 3 days on control cells not receiving any treatment. 1 hour after the infection, the test product (AmB or DABF-AmB) is added at concentrations ranging from 0.03 to 100 µM. The percentage inhibition of the cytopathogenic effect is determined as follows:

$$\frac{[OD \text{ (treated infected cells)} - OD \text{ (infected cells)}]}{[OD \text{ (healthy cells)} - OD \text{ (infected cells)}]}$$

Under these conditions, AmB has no detectable antiviral activity and is cytotoxic at concentrations above 5 µM. In contrast, DABF-AmB completely inhibits the cytopathogenic effects of the virus from 10 µM upwards [$IC_{50}$ (50% inhibition of the cytopathogenic effect)= 5 µM], and no cytotoxic effect was observed for DABF-AmB after treating the cells with 20 µM for 4 weeks. N-methylglucamine and benzylidene glucoside have no effect on the virus.

have just been described more explicitly; on the contrary, it embraces all the variants which may come to the mind of a specialist in this field without departing from the framework or the scope of the present invention.

I claim:

1. A method for inhibiting the multiplication cycle of a viral agent in host cells wherein said multiplication cycle entails a serine protease comprising:
    contacting said viral agent and host cells with an effective serine protease inhibiting amount of a compound of formula (I)

where $R_1$ represents a polyene macrolide of amphotericin B, $R_2$ represents a hydrogen atom or a methyl group, and $R_3$ represents a methyl, ethyl, propyl or phenyl group.

2. The method of claim 1, wherein the compound of formula (I) is 1-deoxy-1-amino-4,6-O-benzylidene-D-fructosyl-AmB.

3. The method of claim 1, wherein said compound is used at a concentration from 1 mM to 100 mM.

* * * * *